United States Patent
Lampert et al.

(10) Patent No.: US 9,889,262 B2
(45) Date of Patent: Feb. 13, 2018

(54) INSUFFLATION SYSTEM AND METHOD FOR OPERATING THE INSUFFLATION SYSTEM

(71) Applicant: Storz Endoskop Produktions GmbH, Tuttlingen (DE)

(72) Inventors: Hugo Lampert, Diessenhofen (CH); Fabian Pilatus, Constance (DE); Peter Ruh, Gottmadingen (DE)

(73) Assignee: Storz Endoskop Produktions GmbH, Tuttlingen (DE)

(*) Notice: Subject to any disclaimer, the term of this patent is extended or adjusted under 35 U.S.C. 154(b) by 195 days.

(21) Appl. No.: 14/663,652

(22) Filed: Mar. 20, 2015

(65) Prior Publication Data
US 2015/0265784 A1    Sep. 24, 2015

(30) Foreign Application Priority Data

Mar. 21, 2014  (DE) .................. 10 2014 103 941

(51) Int. Cl.
*A61M 37/00*  (2006.01)
*A61M 13/00*  (2006.01)
*A61B 1/00*   (2006.01)

(52) U.S. Cl.
CPC ....... *A61M 13/003* (2013.01); *A61B 1/00006* (2013.01); *A61B 1/00068* (2013.01); *A61M 2202/02* (2013.01); *A61M 2205/3334* (2013.01)

(58) Field of Classification Search
CPC .. A61M 13/00; A61M 13/003; A61M 13/006; A61M 2202/02;
(Continued)

(56) References Cited

U.S. PATENT DOCUMENTS 4,800,869 A    1/1989  Nakajima
6,076,520 A *  6/2000  Cooper ............ A61M 16/0063
                                            128/200.14
(Continued)

FOREIGN PATENT DOCUMENTS

DE    102009048994 A1    4/2011
WO       2007050516 A2   5/2007
WO       2008122969 A1  10/2008

OTHER PUBLICATIONS

English Translation of Extended European Search Report Application No. 15158749.0 Completed: Jul. 17, 2015; dated Sep. 17, 2015 4 pages (translation)

*Primary Examiner* — Kevin C Sirmons
*Assistant Examiner* — Leah Swanson
(74) *Attorney, Agent, or Firm* — Whitmyer IP Group LLC

(57) ABSTRACT

An insufflation system has a medical instrument, which has a channel through which an insufflation gas can be passed from the proximal end to the distal end. A first valve in the instrument can be switched between a first switching state and a second switching state. It is proposed that a pressure sensor be provided which is connected to the channel and which can detect the two switching states of the first valve. A second switch-over valve can be switched by a control unit in accordance with the detected pressure values, such that the instrument can be connected by the second switch-over valve either to a source of insufflation gas or to a source of air. The second switch-over valve is designed such that only air is delivered in the first switching state of the first valve and only insufflation gas is delivered in the second switching state.

15 Claims, 5 Drawing Sheets

(58) Field of Classification Search
CPC .. A61M 2202/0225; A61M 2205/3334; A61B 1/00006; A61B 1/00068
USPC .......................................................... 604/26
See application file for complete search history.

(56) References Cited

U.S. PATENT DOCUMENTS

| | | | |
|---|---|---|---|
| 7,824,329 B2 * | 11/2010 | Aizenfeld | A61B 1/00154 600/156 |
| 2007/0238929 A1 * | 10/2007 | Aizenfeld | A61B 1/015 600/158 |
| 2008/0262311 A1 * | 10/2008 | Itou | A61B 1/00039 600/152 |
| 2011/0086332 A1 | 4/2011 | Speiser et al. | |
| 2012/0016293 A1 | 1/2012 | Hayashi | |

* cited by examiner

INSUFFLATION SYSTEM AND METHOD FOR OPERATING THE INSUFFLATION SYSTEM

FIELD OF THE INVENTION

The invention relates to an insufflation system with a medical instrument which has a channel through which an insufflation gas can be guided from the proximal end to the distal end. The instrument has a valve which is arranged in the channel. In a first switching state the valve leads the insufflation gas off to the environment and, in a second switching state, guides the insufflation gas through channel within the instrument. An insufflator supplies the insufflation gas to the channel.

BACKGROUND OF THE INVENTION

The invention further relates to a method for operating an insufflation system.

An insufflation system of this kind is known from WO 2007/050516 A and such a valve is known from DE 10 2009 048 994 A1.

Insufflation systems are used in the medical field for the purpose of inflating hollow cavities in the body, such that endoscopic procedures, for example inspections or interventions, can be carried out in the body cavities with a better view.

Inspections of this kind are, for example, examinations of the gastrointestinal tract, for example in preventive medical examinations of the rectum and large intestine. Another widespread area of use is laparoscopy of the abdominal space.

An insufflation system of this kind consists, in the first instance, of a medical instrument that can be inserted into the body cavities and that has a channel through which an insufflation gas can be guided from the proximal end to the distal end. The insufflation gas is made available by an insufflator, which is connected to the proximal end of the medical instrument during use.

The insufflator supplies the instrument with a defined volumetric flow that is suitable for the respective procedure, i.e. a defined amount of insufflation gas is moved through the instrument by the insufflator. The so-called flow rate is usually given in l/min. At the same time, a defined insufflation pressure can be set, so as to be able to adapt this to the respective anatomical circumstances.

Air was initially used as insufflation gas, but it was found that air is poorly resorbed by the body, and postoperative effects are caused by the high nitrogen content of the air.

Therefore, air is increasingly no longer used as insufflation gas and is replaced by other gases, in particular carbon dioxide ($CO_2$), which can be very quickly resorbed by the living body and can be eliminated in the breath.

Therefore, within the meaning of the present invention, the term "insufflation gas" refers to those gases that are suitable for insufflation of body cavities, but not to air.

Carbon dioxide as insufflation gas is unproblematic from the medical point of view and can also be delivered in relatively large quantities to the body, even in protracted examinations or interventions. However, the carbon dioxide that can be used in the medical field is relatively expensive.

In an actual insufflation procedure, i.e. the inflation of body cavities, quantities of insufflation gas of, for example, 1-3 l/min are delivered at pressures of approximately 350 mmHg.

In the so-called standby mode, for example approximately 5 l/min are delivered at a pressure of approximately 80 mmHg.

In the insufflation system mentioned at the outset, the various states are controlled by means of a so-called bypass valve being arranged in the channel of the instrument. This bypass valve has, firstly, a passage arranged in the flow path of the channel. Secondly, a branch line leading to the environment is present in the valve. This branch line ends in a head of a manually movable valve head piece and the mouth of this branch line lies in the area of the head.

In a first switching state of the valve, this branch line is open. That is to say, insufflation gas delivered from the insufflator flows through the branch line and therefore escapes to the environment through the valve. The channel within the medical instrument is still open, but it provides a remarkable flow resistance to the approaching insufflation gas. As a result the insufflation gas flows through the branch line in the valve to the environment and not through the channel distally to the valve. That corresponds to the standby mode.

The valve is designed such that the outlet opening of the branch line can be closed when a person holding and operating the instrument places a finger on the opening. By closing the branch line, only the channel in the instrument is open. The gas now has to flow through a long and mostly thin flow channel to the patient, for which reason a greater resistance has to be overcome. The higher flow resistance causes a pressure increase in the system.

This corresponds to the second switching state of the valve, in which it is now possible for the insufflation gas from the insufflator to be passed exclusively through the channel of the instrument.

When the outlet opening of the branch line of the valve is freed again by removing the finger that was closing it, the insufflation gas can again be discharged to the environment via the valve. The pressure in the system then drops again. These pressure differences can be used to identify the different switching states of the first valve.

However, a disadvantage of such an insufflation system is that the relatively expensive insufflation gas, in particular carbon dioxide, flows continuously out of the system via the valve in the instrument in the first switching state and is thus lost for the actual insufflation procedure. Consequently, measures have to be taken to reduce these quantities of carbon dioxide that are lost.

US 2012/0016293 A1 discloses an endoscope gas delivery system having a carbon dioxide gas cylinder for delivering the insufflation gas. When the remaining amount of the carbon dioxide gas of the cylinder is detected and the detected pressure of the carbon dioxide becomes less than a predetermined value an air pump is rotated to supply pressurized air to the body.

It is therefore an object of the present invention to remedy this situation and to further develop an insufflation system in such a way that it can be operated more economically and more safely, in particular with savings being made in terms of expensive insufflation gas.

SUMMARY OF THE INVENTION

According to the Invention, the object is achieved by an insufflation system comprising a medical instrument having a channel for guiding an insufflation gas therethrough from a proximal end to a distal end of said medical instrument, a first valve connected to said channel, said first valve having a first switching state and a second switching state, in said second switching state said first valve allows insufflation gas passing through said channel only, and in said first switching state allowing insufflation gas to escape through said first valve to the environment, an insufflator for providing and feeding an insufflation gas to said proximal end of said channel, a pressure sensor connected to said channel proximally to said first valve for detecting said first and said second switching state of said first valve, a second switch-over valve arranged upstream of said first valve in terms of a flow of said insufflation gas, said second switch-over valve having a first input connected to the source of said insufflation gas and a second input connected to a source of air, and having an output connected to said channel, and a control unit connected to said pressure sensor for processing pressure values dates detected by said pressure sensor and connected to said second switch-over valve, said control unit switches said second switch-over valve to a connection between said second input and said output for passing air when said pressure sensor detects said first switching state of said first valve for feeding air instead of insufflation gas through said channel and said first valve, and said control unit switches said second switch-over valve to a connection between said first input and said output for passing insufflation gas when said pressure sensor detects said second switching state of that first valve for feeding insufflation gas through said channel.

These measures have the advantage that, in the operating phases in which the first valve of the instrument is in the first switching state, air instead of insufflation gas is conveyed through the system and is discharged to the environment through the first valve.

In this first switching state, which is present for most of the duration of an intervention, it is therefore only air that is conveyed through the first valve and discharged into the environment, not the expensive and sometimes problematic insufflation gas. If an actual insufflation procedure is then to be carried out, the branch line in the first valve is closed and the pressure in the system rises, which is detected by the pressure sensor. The corresponding signal is delivered to the control unit, which detects it and then switches the second switch-over valve such that it becomes connected to the source of insufflation gas, with the result that, in the second switching state of the first valve, insufflation gas instead of air then flows through the channel of the medical instrument to the distal end thereof.

It is thus advantageously ensured by simple measures that, during the actual insufflation procedure, it is almost exclusively insufflation gas that is introduced into the body cavity. In the first switching state, in which considerable amounts of gas are discharged from the first valve over a relatively long period of time, air instead of insufflation gas flows through the system and escapes to the environment through the branch line of the first valve. This air that flows out can mix with the air in the operating area and is entirely unproblematic.

In a further embodiment of the invention, the pressure sensor, the second switch-over valve and the control unit are arranged in the insufflator.

This measure has the considerable advantage that the detecting, controlling and switching elements are arranged in the insufflator, such that already existing instruments can also be attached to such an insufflator. Instruments of this kind are designed for long operating periods and are therefore produced from corresponding high-quality materials and are accordingly expensive. The equipment present on these instruments, i.e. the channel passing through the instrument and the first valve which is arranged in said channel and can be brought to the first and second switching state, can now be combined with the structural parts according to the invention. It is possible in principle to arrange at least the pressure sensor and second switch-over valve also in an instrument. For this purpose, however, the design of the instrument would have to be accordingly modified. By providing the pressure sensor and the second switch-over valve and also the control unit in the insufflator, already existing medical instruments can be connected to an insufflator equipped according to the invention, such that the overall system can then work according to the invention. The pressure sensor is always arranged proximally to the first valve. The invention can therefore be realized very economically.

In a further embodiment of the invention, the source of air has a compressor, which sucks in ambient air and feeds the latter to the channel of the instrument.

This measure has the considerable advantage that ambient air is used which is available in sufficient quantity in operating theaters and is also of medically safe quality. The compressor sucks in this ambient air and brings it to the suitable pressure and then conveys it at the desired flow rate through the instrument. This also leads to an extremely economic and also ergonomic implementation of the invention. In hospitals, supply lines for air are also present, for example for respiratory processes, to which lines the source of air can be attachable.

In a further embodiment of the invention, the compressor is arranged in the insufflator.

This measure has the advantage that a particularly compact appliance can be made available, such that no measures causing structural protrusions are needed at the site of use.

In a further embodiment of the invention, the first valve of the instrument has a branch line, which is open to the environment and which is connected to the channel.

This measure known per se has, in combination with the invention, the advantage that the control can be performed very easily between the switching states, and the associated pressure differences can be detected by the pressure sensor by structurally simple measures, since this pressure sensor is arranged upstream of the first valve in the channel and can detect these pressure differences.

In a further embodiment of the invention, the branch line has an outlet opening to the environment, which outlet opening can be closed by the finger of a person handling it.

This measure known per se also ensures, in combination with the inventive measures, a simple switching between the first and second switching state, which is detected by the pressure sensor and can be converted via the control unit to a switching of the second switch-over valve.

In a further embodiment of the invention, the first valve of the instrument can be brought to a third switching state in which insufflation gas or air is blocked from passing through, but a further passage of the first valve is opened, and wherein the stream of air can be guided into a storage vessel with a flushing liquid, and the further passage is connected to an outlet of the storage vessel, such that, in the third switching state of the first valve, flushing liquid can be conveyed through the instrument from the proximal end to the distal end via the air.

Although it is already known per se to bring such a first valve to the third switching state, it is now possible according to the invention to use air, instead of the expensive insufflation gas, to convey the flushing liquid. This combination also results in an especially economic operation of the insufflation system.

In a further embodiment of the invention, the control unit has a hysteresis circuit which delays a switching of the second switch-over valve in case of change of the first valve from the first switching state to the second switching state due to a pressure drop detected by the pressure sensor.

This measure takes account of the customary practice of physicians in performing several insufflation procedures in short succession at the start of an intervention, in order to inflate the body cavities gradually to a defined degree. Since these insufflation procedures take place at an interval of a few seconds, this time delay provided by the hysteresis circuit ensures that no brief switching procedures between delivery of insufflation gas and delivery of air takes place that would be ended again after one or two seconds.

After a certain state of inflation has been reached, the appliance is often operated for quite a long time in the first switching state of the first valve, and it is only occasionally that a new insufflation procedure is performed, for example if there is a poor view of the body cavity or if the available space is confined.

The insufflation system according to the invention is therefore in principle operated using the following steps, namely:
  detecting the switching state of the first valve by means of a pressure sensor arranged proximal to said first valve,
  delivering pressure signals detected by said pressure sensor to a control unit,
  switching the second switch-over valve, by means of the control unit, to allow delivery of insufflation gas when the second switching state of the first valve is detected, and
  switching the second switch-over valve to allow delivery of air to the first valve when the first switching state of the latter is detected.

In practice, it is advantageous for the switching of the second switch-over valve to be performed with a time delay, when a change of the first valve from the first switching state to the second switching state is detected.

The method can be performed particularly economically if the air to be delivered is compressed in the insufflator.

It will be appreciated that the aforementioned features and the features still to be explained below can be used not only in the cited combinations but also in other combinations or singly, without departing from the scope of the present invention.

BRIEF DESCRIPTION OF THE DRAWINGS

The invention is described and explained in more detail below with reference to the attached drawings, in which.

DETAILED DESCRIPTION OF THE INVENTION

The principal structural elements of the insufflation system will first of all be described with reference to FIGS. 1 and 2.

Figure 1:
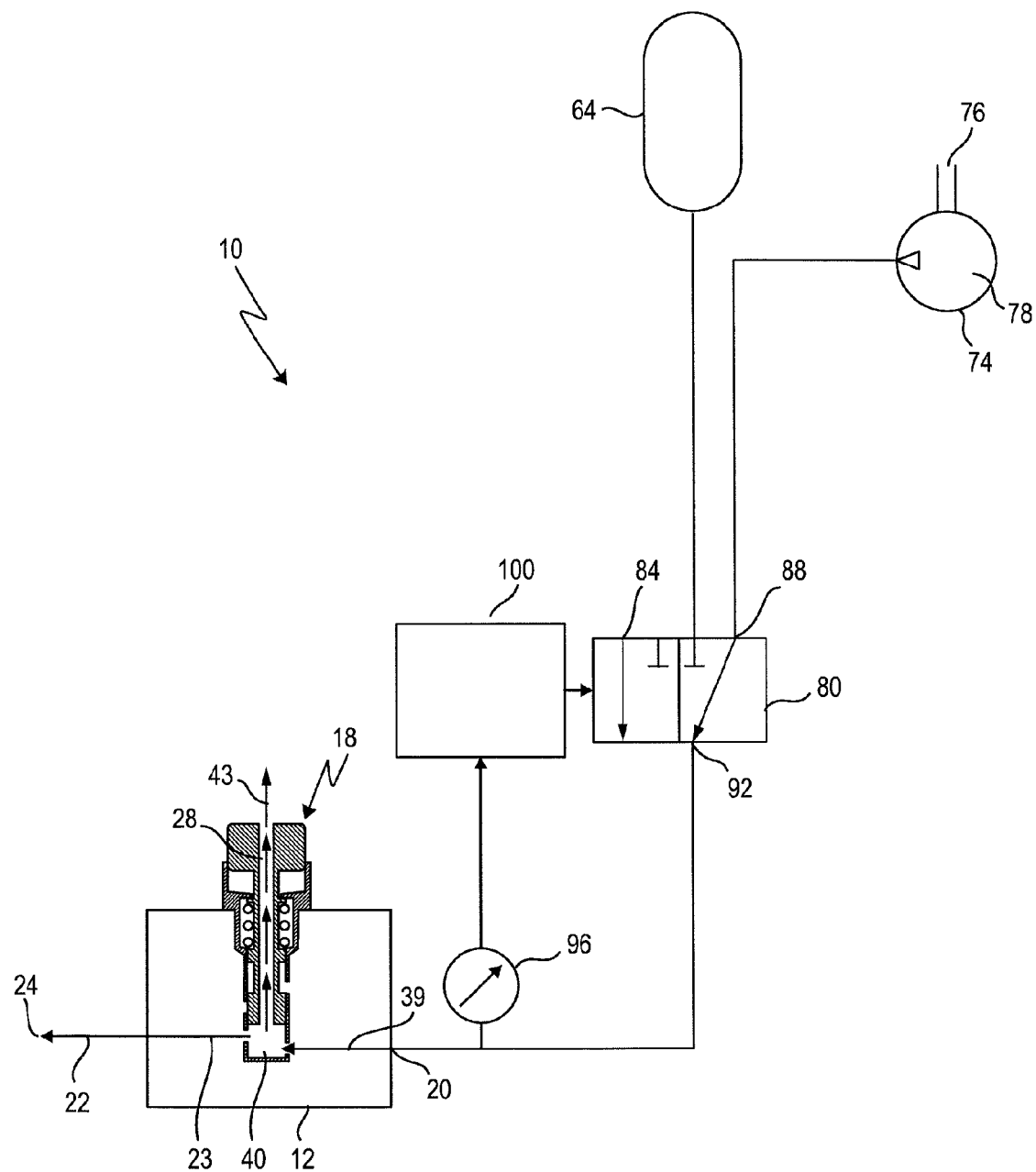
FIG. 1 shows, in a very schematic form, the principal structural elements of an insufflation system according to the invention.

An insufflation system shown in FIG. 1 is designated in its entirety by reference number 10.

The insufflation system 10 has a medical instrument 12, which is designed, for example, as a colonoscope.

The medical instrument 12 has a channel 23 through which gaseous or liquid media can be guided from a proximal port 20 to a distal port 24. In a colonoscope, a long flexible shaft 22 is present which can be inserted through the anus in order to examine the intestinal tract.

A first valve 18 is arranged communicating with the channel 23. The precise design and the different operating states of the first valve 18 will first be described with reference to FIGS. 2a to 2c.

The first valve 18 has a housing 30 in which a first valve body 26 is received so as to be able to move to and fro. A bore 28 extends longitudinally all the way through the body 26. On its outer side, the body 26 has an outer annular flange 27, which can abut against an underside of an inner annular flange 32 of the housing 30. A spring 34, which is arranged in a space between the outer side of the body 26 and the inner side of the housing 30, is pretensioned in such a way that it presses the body 26 into the position shown in FIG. 2a. In doing so, it is supported, at one end, on a lower, inwardly directed projection (not shown in detail here) of the housing 30 and, at the other end, on the underside of the outer annular flange 27 of the body 26.

An inlet opening 38 is present at the lower end of the housing 30, and an outlet opening 42 is arranged lying opposite said inlet opening 38.

A chamber 40 is located between the two openings 38 and 42.

Figure 2A:
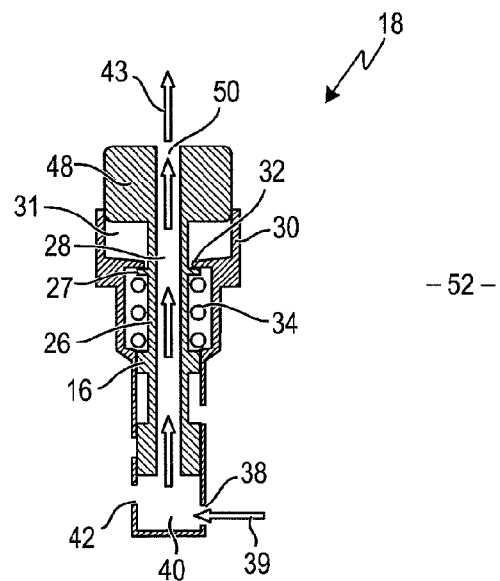
FIG. 2 shows the first valve of the instrument, in the first switching state in FIG. 2a, in the second switching state in FIG. 2b, and in the third switching state in FIG. 2c.

In the state shown in FIG. 2a, a lower end of the body 26 forms an upper end of the chamber 40. The housing 30 is inserted into the instrument 12 in such a way that the inlet opening 38 and the outlet opening 42 are connected to the channel 23 in terms of flow.

At the upper end in the view in FIG. 2, the body 26 is provided with a radially widened headpiece 48, which is received in a corresponding recess 31 at the upper end of the housing 30. As has been described before, the bore 28 also extends all the way through the headpiece 48 and ends in an outlet opening 50.

As can be seen from FIG. 2a, the headpiece 48 protrudes slightly above the housing 30 in the operating state shown in FIG. 2a.

This operating state of the first valve 18 shown in FIG. 2a is a first switching state 52.

In this first switching state 52, a gaseous medium, as indicated by the arrow 39, enters the chamber 40 via the inlet opening 38. The delivered gaseous medium 39 passes through the first valve 18 to the environment by way of the bore 28, open to the outside, in the first valve body 26. It does this because the flow resistance of the long channel 23 to the patient is much greater than the flow resistance in the bore 28. Therefore, the entire gas stream 43 flows out through this branch line of the first valve 18.

Figure 2B:
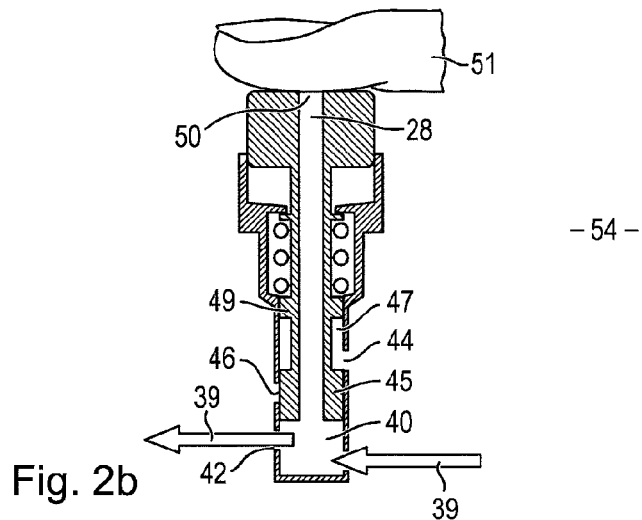

FIG. 2b shows a situation in which a finger 51 is placed on the top of the headpiece 48 of the first valve body 26, specifically in such a way that the outlet opening 50 of the bore 28 is closed.

In this switching state, which constitutes a second switching state 54 of the first valve 18, the gas quantity 39 delivered to the first valve 18 now flows through the chamber 40 and out of the outlet opening 42, i.e. the gas quantity 39 delivered is guided in its entirety through the first valve 18 and the channel 23.

In this second switching state 54, the insufflation gas 39 is guided all the way through the first valve 18 into the channel 23 as far as the distal end thereof, i.e. to the outlet 24, specifically with the desired flow rate and the desired pressure, for example with a quantity of insufflation gas of 1-3 l/min passed through at a pressure of 350 mmHg.

Figure 2C:
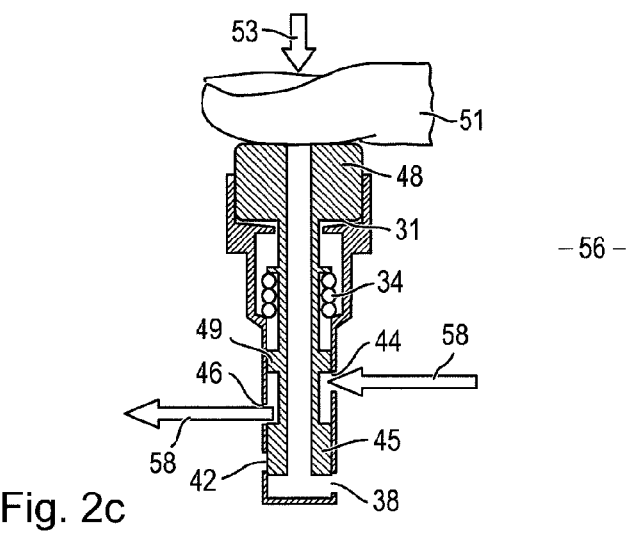

FIG. 2c shows a third switching state 56 of the first valve 18. In this switching state, the finger 51 of the operator has moved the first valve body 26 "down" counter to the force of the spring 34, specifically until the headpiece 48 has moved to the maximum extent into the recess 31 in the housing 30.

In this third switching state 56, a lower piston portion 45 of the first valve body 26 has been pushed in front of the outlet opening 42.

It is thus no longer possible for gas quantities to pass through the first valve 18 via the inlet opening 38 of the housing 30. On the one hand, the bore 28 is closed by the placement of the finger 51, and, on the other hand, the outlet opening 42 is closed by the piston portion 45.

In the third switching state 56, a flushing stream inlet opening 44 arranged above the inlet opening 38 is opened, as is a flushing stream outlet opening 46 on the output side. In this area, the first valve body 26 has a smaller external diameter than in the area of the piston portion 45. In this way, a so-called flushing stream chamber 47 is created, of which the upper end forms a further piston portion 49, of increased diameter, of the first valve body 26.

As is shown in FIG. 2c, a flushing stream 58 composed for example of a liquid medium, can now be established which enters the flushing stream chamber 47 via the open flushing stream inlet opening 44 and leaves the first valve 18 again via the flushing stream outlet opening 46. Depending on the design of the instrument, the flushing stream 58 can pass directly into the channel 23 downstream from the first valve 18 or, if appropriate, into a separate flushing stream channel. In this way, in the third switching state as shown in FIG. 2c, a flushing stream can be guided through the instrument 12 from the proximal end to the distal end via the first valve 18.

The flushing medium, in most cases a liquid flushing solution, delivered to the human or animal body can then be suctioned off via a suction line (not shown in detail here) of the instrument.

When the first valve 18 is freed again from the switching state shown in FIG. 2c, i.e. when the finger 51 is completely removed from the headpiece 48, the spring 34 pushes the first valve body 26 into the switching state 52 shown in FIG. 2a.

Returning now to FIG. 1, the first valve 18 is shown there in the first switching state 52. According to the invention, a pressure sensor 96 is provided which is connected to the channel 23 in flow terms and which detects the pressure conditions prevailing in the channel. The pressure sensor 96 is connected to a control unit 100, which detects and processes the signal output by the pressure sensor 96. The pressure sensor 96 is arranged proximally or upstream to the first valve 18.

Furthermore, a second switch-over valve 80 is provided which, by way of its output 92, is likewise connected in flow terms to the channel 23.

On the input side, the second switch-over valve 80 is connected by a first input 84 to a source of insufflation gas 64. In practice, this is a gas cylinder, or a central or in-house supply, which contains compressed carbon dioxide prepared and suitable for the medical sector. The second switch-over valve 80 also has a second input 88, which is connected to a source 78 of air.

The source of air 78 has a compressor 74 which sucks in air from the environment via an intake tube 76 and compresses the air. The air can also originate from a central in-house supply.

As can be seen from FIG. 1, the control unit 100 switches the second switch-over valve 80 to an operating state in which the input 88 of the second switch-over valve 80 is connected to the source of air 78 if the first valve 18 in the medical instrument 12 is located in the first switching state 52. In this state, as has been described before, it is exclusively air from the source of air 78 that is guided via the second switch-over valve 80 to the port 20 of the instrument 12. The air flows back out through the bore 28. If the first valve 18 is now brought to the second switching state 54 as shown in FIG. 2b, a pressure increase takes place in the channel 23. This pressure increase can be detected by the pressure sensor 96 and sends a corresponding pressure signal to the control unit 100.

When the control unit 100 detects this pressure increase, for which a defined threshold value has to be exceeded here for reasons of circuitry, as will be described below, it sends a switching signal to the second switch-over valve 80, such that the latter switches to enable flow of insufflation gas, i.e. carbon dioxide. As a result of the design as a solenoid valve, a corresponding structural part, e.g. a rocker or a piston, is moved, which ensures that the first input 84 is connected to the source 64 of insufflation gas and is then connected to the output 92. In this switching state, air can then no longer flow through the input 88 to the output 92. An insufflation procedure can now be performed in this switching state.

This can be performed, for example, with a flow rate of 1-3 l/min of insufflation gas at a pressure of 350 mmHg.

When the first valve 18 adopts its first switching state 52 again, as has been described before, this is associated with a corresponding pressure drop, which is again detected by the pressure sensor 96. The signal from the latter is then processed by the control unit 100 and is used to switch the second switch-over valve 80 back to enable air to pass through, as is shown in FIG. 1.

The structural elements in the form of pressure sensor 96 and second switch-over valve 80 can also be integrated in the instrument 12. In principle, the control unit 100 could also be integrated in the medical instrument, in which case corresponding connections to the source 64 of insufflation gas and to the source 78 of air would have to be provided.

It is also possible to integrate only the pressure sensor 96 and the second switch-over valve 80 in the instrument 12 and to assign the control unit 100 to a separate appliance, namely an insufflator.

Figure 3:
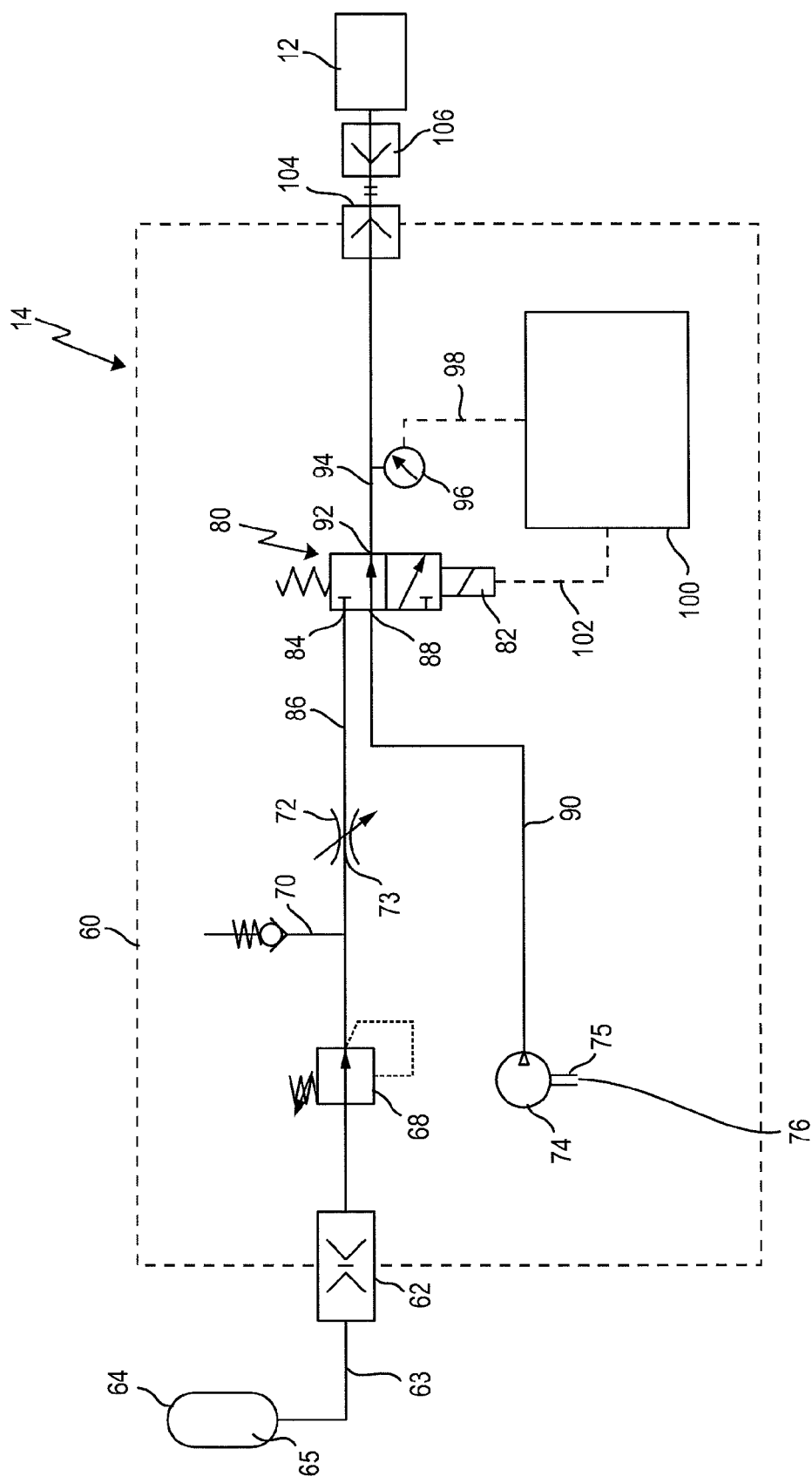
FIG. 3 shows an illustrative embodiment of an insufflation system.

FIG. 3 shows a variant of the insufflation system 10 according to the invention, in which the above-described structural parts are received in an insufflator 14 which, on the output side, has an instrument port 104. A corresponding port 106 of an instrument 12, which is equipped with a first valve 18 as described before, can be connected to this instrument port 104. The insufflator 14 shown in FIG. 3 has a port 62 by means of which it can be connected by a line 63 to a source 64 of insufflation gas.

The latter can be a gas cylinder 65 which receives the insufflation gas, in most cases carbon dioxide, compressed at a relatively high pressure. An in-house or central supply is customary in hospitals.

The insufflator 14 accommodates a pressure regulator 68, by means of which it is possible to adjust the pressure desired for the medical intervention or the pressure desired for operating the medical instrument 12

A safety first valve 70 arranged downstream ensures that high gas pressures are not inadvertently delivered by the instrument 12 to a human body in the event of a failure of the pressure regulator 68. Arranged downstream from the safety first valve 70 is a flow regulator 72 with a nozzle 73 by which the respective flow rates are adjustable. Here, it is also possible to provide several gas paths connected in parallel, with nozzles sitting in each of them in order to effect certain predefined flow rates. This gas line is connected by a line 86 to the first input 84 of a second switch-over valve 80, which is here designed as a solenoid first valve 82.

The insufflator 14 moreover accommodates a compressor 74, which sucks in ambient air 76 through an intake tube 75 and accordingly compresses the air.

The output of the compressor 74 is connected by a line 90 to the second input 88 of the second switch-over valve 80.

The solenoid first valve 82 is connected by a control line 102 to a control unit 100.

Downstream from the second switch-over valve 80, i.e. after its output 92, a pressure sensor 96 is arranged in the line 94 leading to the instrument port 104. The pressure signal from the pressure sensor 96 is fed to the control unit 100 via a control line 98.

In FIG. 3, the dashed line indicates a housing 60 of the insufflator 14, i.e. all the structural parts described above are accommodated in the insufflator. Only the gas cylinder 65 is arranged outside the housing 60, so that the former can be replaced if necessary.

During the operation of the insufflation system 10, a medical instrument 12 is connected by its port 106 to the instrument port 104 of the insufflator 14. The instrument 12 has the first valve (not shown).

The corresponding power supply, i.e. electrical power supply, and the corresponding logic circuit in the control unit 100 are not shown here.

Thus, the insufflation system 10 is then ready for operation.

The function pattern of the different operating states will be explained with reference to the graphs in FIG. 4. The top graph shows the pressure in the insufflator over time. In the first switching state 52 of the first valve, a pressure below a defined switching threshold 57 prevails in the insufflator.

If the pressure is approximately 80 mmHg, the switching threshold 57 can be approximately 120 mmHg, such that situation-dependent pressure fluctuations in the first switching state 52 of the first valve can be left out of consideration.

The second, middle graph shows the switching state of the second switch-over valve 80 over time, wherein a switching state 108 represents a state in which there is no flow of insufflation gas, i.e. $CO_2$, but exclusively air.

Figure 4:
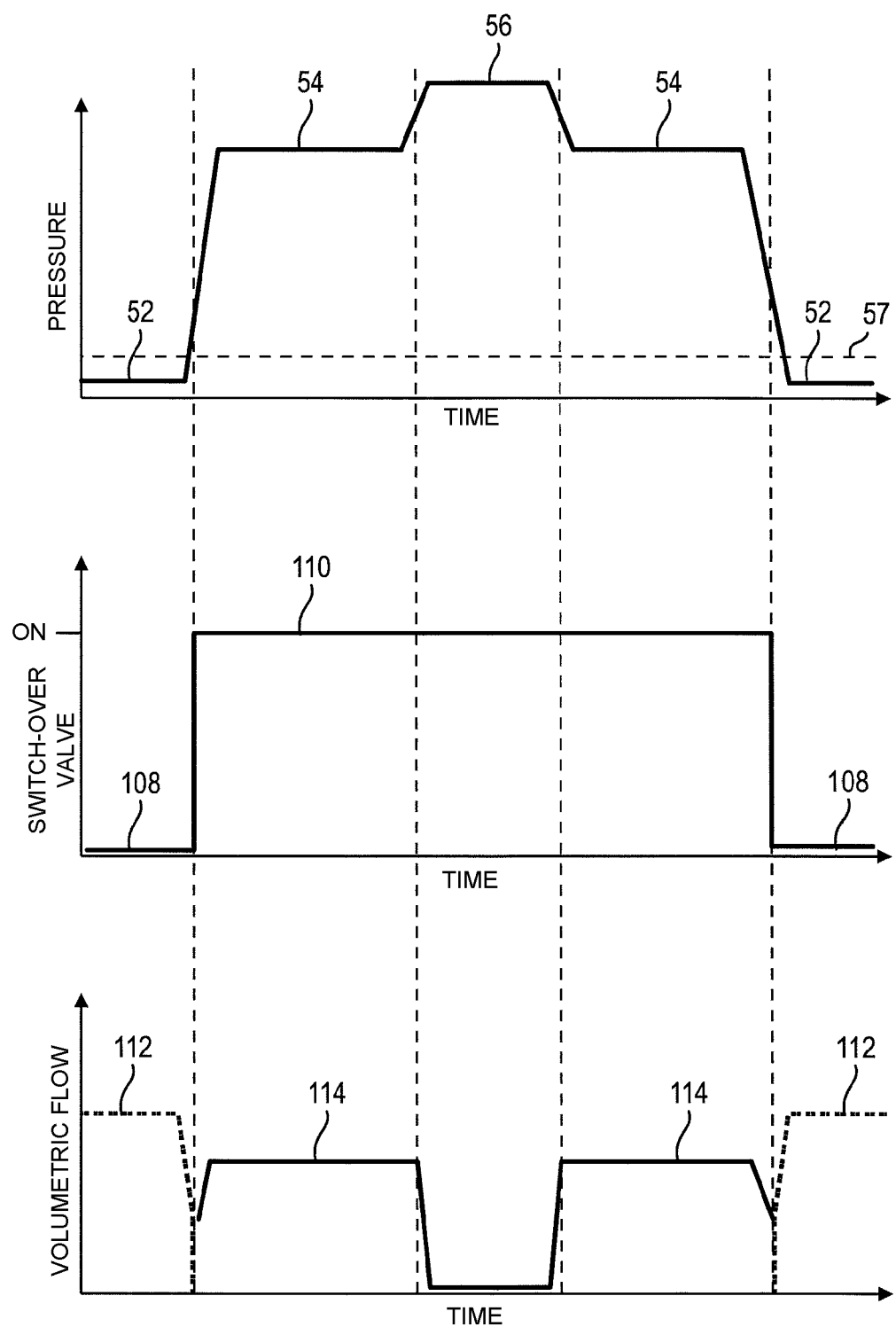
FIG. 4 shows three graphs to explain the operating parameters in the different operating states, the first graph showing the pressure over time, the second graph showing the switching state of the second switch-over valve over time, and the third graph showing the volumetric flow over time.

The bottom graph in FIG. 4 shows the respective volumetric flow of media flowing through the system. The dashed line indicates the air flow, and the solid line indicates the flow of insufflation gas.

In the first switching state 52 of the first valve 18 and the switching state 108 of the second switch-over valve, only air 112 flows through the instrument 12.

If the first valve 18 is now brought to the second switching state 54, the pressure at the instrument inlet increases, since now the entire gas quantity delivered has to be guided through the instrument and can no longer escape through the first valve. This pressure increase is detected by the pressure sensor 96, and the second switch-over valve 80 is switched to the switching state 110 by the control unit 100, i.e. the second switch-over valve 80 is now switched for exclusive flow of insufflation gas, i.e. $CO_2$. As can be seen from the bottom graph, the volumetric flow of air 112 thus decreases and, at the same time, the volumetric flow of insufflation gas 114, i.e. $CO_2$, increases to a defined level. An insufflation procedure is performed in this state.

If the first valve 18 in the instrument 12 is now brought to the third switching state 56, the pressure further increases, since no gaseous medium now passes through the first valve 18, as has been described with reference to FIG. 2c.

In this state, the second switch-over valve is still open, and the flow of gas, here the flow of the insufflation gas, can be used to guide a flushing liquid through the instrument. In this way, the volumetric flow correspondingly decreases, since the latter is only used to discharge and carry the flushing liquid. When the first valve 18 is brought to the second operating state 54 again, only insufflation gas 114 is guided through the instrument.

When the first valve 18 is fully released, i.e. when the finger 51 is lifted from the outlet opening 50, the pressure drops sharply, going below the switching threshold 57. The second switch-over valve then switches to the state 108, in which once again only air is guided through the instrument, such that the flow of air 112 then once again increases correspondingly.

Figure 5:
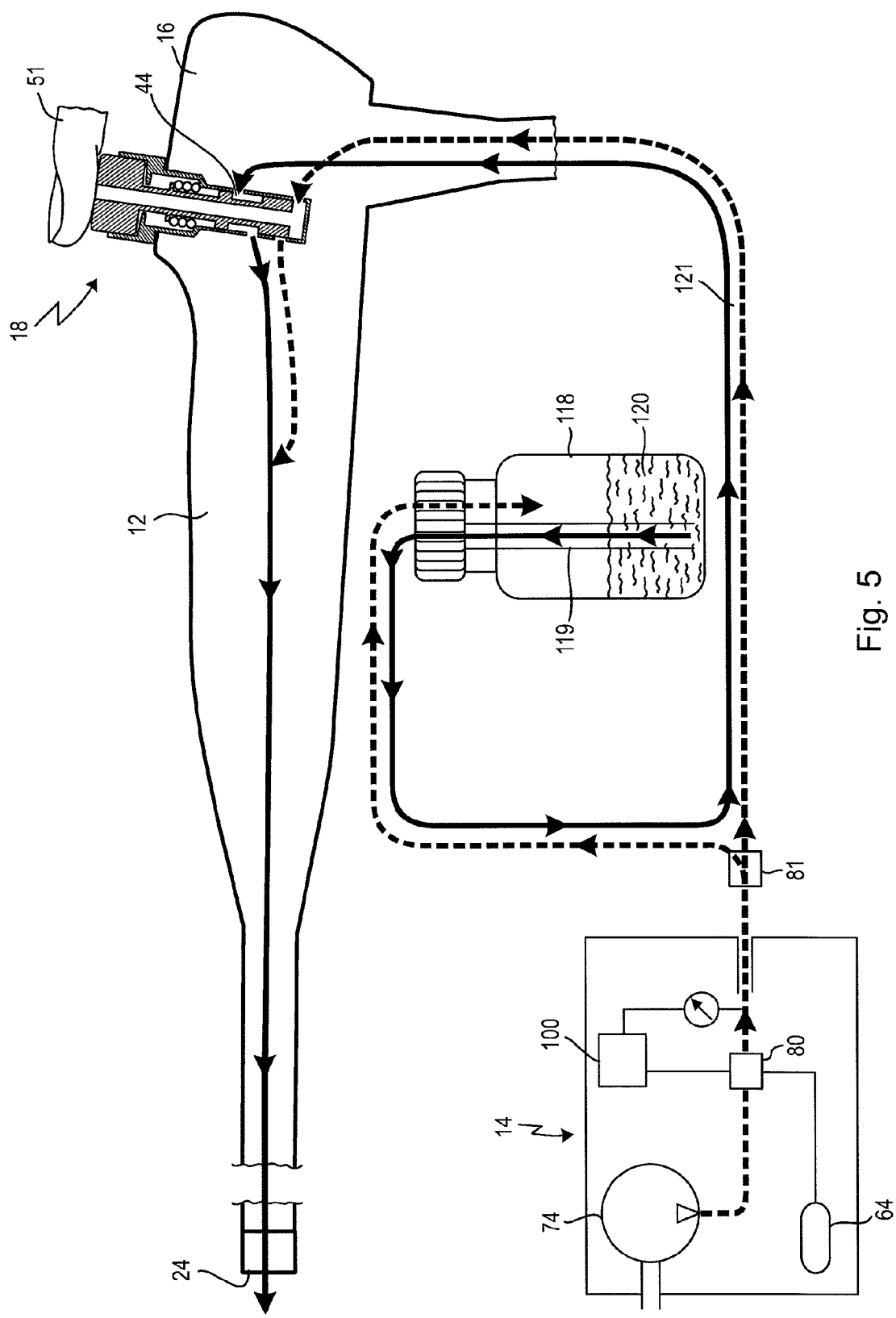
FIG. 5 shows, in a very schematic form, a further illustrative embodiment of an insufflation system according to the invention, in which an already existing instrument is depicted with an insufflator and a flushing system.

It will be seen from FIG. 5 that the medical instrument 12 shown there is a conventional instrument, namely a colonoscope, which is provided with a first valve 18. In FIG. 5, the first valve 18 is in the third switching state 56. By way of a junction 81, the gas stream coming from the insufflator 14 can be led into a vessel 118 in which a flushing liquid 120 is received.

An ascent line 119 is immersed in the flushing liquid 120 and is connected by a line 121 to the flushing stream inlet opening 44 of the first valve 18.

In this state, flushing liquid 120 is then guided through the instrument 12 as far as the distal outlet 24 thereof.

It was previously described that the insufflation gas is used to convey the flushing liquid.

Instead of insufflation gas, however, it is also possible in principle to deliver air from the compressor 74.

This means the additional provision of a switching logic that serves exclusively for the "flushing" state. This means that when the first valve 18 is located in the third switching state 56, as is shown in FIG. 2c, the control unit 100 can switch the second switch-over valve 80 to the state in which only air is carried through, which then serves to expel the flushing liquid 120 from the vessel 118.

In FIG. 5, the dashed line indicates the flow of air, while the solid line indicates the flow of flushing liquid.

What is claimed is:

1. An insufflation system comprising
   a medical instrument having a channel for guiding an insufflation gas therethrough from a proximal end to a distal end of said medical instrument,
   a first valve connected to said channel, said first valve having a first switching state and a second switching state, in said second switching state said first valve allows insufflation gas passing through said channel only, and in said first switching state allowing insufflation gas to escape through said first valve to an environment, wherein said channel passed through said first valve in said second switching state, an insufflator for providing and feeding an insufflation gas to said proximal end of said channel, a pressure sensor connected to said channel proximally to said first valve for detecting said first and said second switching state of said first valve, a second switch-over valve arranged upstream of said first valve in terms of flow of said insufflation gas, said second switch-over valve having a first input connected to a source of said insufflation gas and a second input connected to a source of air, and having an output connected to said channel, and a control unit connected to said pressure sensor for processing pressure values detected by said pressure sensor and connected to said second switch-over valve, said control unit switches said second switch-over valve to a connection between said second input and said output for passing air when said pressure sensor detects said first switching state of said first valve for feeding air instead of insufflation gas through said channel and said first valve to said medical instrument, and said control unit switches said second switch-over valve to a connection between said first input and said output for passing insufflation gas when said pressure sensor detects said second switching state of that first valve for feeding insufflation gas through said channel to said medical instrument.

2. The insufflation system of claim 1, wherein said pressure sensor, said second switch-over valve and said control unit are arranged within said insufflator.

3. The insufflation system of claim 1, wherein said source of air has a compressor, which sucks ambient air and feeds the latter to said second input of said second switch-over valve.

4. The insufflation system of claim 3, characterized in that said compressor is arranged in said insufflator.

5. The insufflation system of claim 1, wherein said first valve of said instrument has a branch line, which is open to the environment and which is connected to said channel.

6. The insufflation system of claim 5, wherein said branch line has an outlet opening to the environment, which outlet opening can be closed by a finger of a person handling said instrument.

7. The insufflation system of claim 1, wherein said first valve of said instrument can be brought to a third switching state, in which insufflation gas or air is blocked from passing through said first valve, wherein a further passage of the first valve is opened in said third switching state, wherein a stream of air or of insufflation gas can be guided into a storage vessel for a flushing liquid, and wherein said further passage of said first valve is connected to an outlet of said storage vessel, such that, in said third switching state of the first valve, a flushing liquid can be guided through the instrument from the proximal end to the distal end through that further passage.

8. The insufflation system of claim 1, wherein said control unit has a hysteresis circuit which delays a switching of the second switch-over valve in case of a change of said first valve from said first switching state to said second switching state due to a pressure drop detected by the pressure sensor.

9. The insufflation system of claim 1, wherein the first valve comprises a fluidic valve through which the insufflation gas flows in the second switching state.

10. The insufflation system of claim 1, wherein said first valve is arranged between said second switch-over valve and said distal end of said medical instrument in terms of flow of said insufflation gas so that the insufflation gas passes directly through the second switch-over valve prior to reaching the first valve.

11. The insufflation system of claim 1, wherein said second switch-over valve is operable to provide a connection between said second input and said output for passing air when said pressure sensor detects said first switching state of said first valve, and to provide a connection between said first input and said output for passing insufflation gas when said pressure sensor detects said second switching state of said first valve.

12. The insufflation system of claim 1, wherein said first input, said second input, and said output form integral ports of said second switch-over valve.

13. A method for operating an insufflation system having a medical instrument with a channel for guiding an insufflation gas therethrough from a proximal to a distal end, and having a first valve allowing in a first switching state said insufflation gas to escape through said first valve to an environment and allowing said insufflation gas to pass through said channel at a low pressure, and allowing in a second switching state of said first valve to pass insufflation gas through said channel at a higher pressure, and having an insufflator containing a second switch-over valve for alternatively delivering insufflation gas or air to said channel, said method having the steps of:

detecting a switching state of a first valve by means of a pressure sensor arranged proximal to said first valve, delivering pressure signals detected by said pressure sensor to a control unit, switching a second switch-over valve by means of said control unit to enable delivering of insufflation gas to said first valve when its second switching state is detected, and switching said second switch-over valve to enable delivery of air to said first valve when its first switching state is detected.

14. The method as claimed in claim 13, comprising the step of delaying said switch-over of the second switch-over valve at a change of the first valve from the first switching state to the second switching state.

15. The method of claim 13, wherein air to be delivered is compressed within an insufflator.

* * * * *